United States Patent [19]

Riedel

[11] Patent Number: 4,957,795

[45] Date of Patent: Sep. 18, 1990

[54] ABSORBENT ELASTOMERIC WOUND DRESSING

[75] Inventor: John E. Riedel, Hugo, Minn.

[73] Assignee: Minnesota Mining and Manufacturing Company, St. Paul, Minn.

[21] Appl. No.: 469,708

[22] Filed: Jan. 24, 1990

Related U.S. Application Data

[63] Continuation of Ser. No. 194,082, May 13, 1988, abandoned.

[51] Int. Cl.$^5$ .................. A61F 13/46; A61L 15/20; D04H 1/72; B32B 5/04; B32B 5/08

[52] U.S. Cl. .................. 428/74; 428/76; 428/77; 428/283; 428/286; 428/287; 428/298; 428/311.5; 428/317.1; 428/317.9; 428/360; 428/362; 428/369; 428/372; 604/366; 604/367; 604/370; 604/372; 604/373; 604/375; 604/376; 604/378; 604/385.1

[58] Field of Search .............. 428/286, 287, 360, 362, 428/369, 372, 74, 76, 77, 283, 298, 311.5, 317.1, 317.9; 604/366, 367, 370, 372, 373, 375, 376, 378, 385.1

[56] References Cited

U.S. PATENT DOCUMENTS

| | | |
|---|---|---|
| 3,670,731 | 6/1972 | Harmon . |
| 4,100,324 | 7/1978 | Anderson et al. ............ 428/288 |
| 4,118,531 | 10/1978 | Hauser ............ 428/224 |
| 4,209,563 | 6/1980 | Sisson ............ 428/288 |
| 4,366,814 | 1/1983 | Riedel ............ 428/245 |
| 4,379,192 | 4/1983 | Wahlquist et al. ............ 428/156 |
| 4,414,970 | 11/1983 | Berry . |
| 4,429,001 | 1/1984 | Kolpin et al. ............ 428/283 |
| 4,565,736 | 1/1986 | Stein et al. ............ 428/286 |
| 4,650,479 | 3/1987 | Insley ............ 604/358 |
| 4,660,228 | 4/1987 | Ogawa et al. ............ 2/168 |
| 4,692,368 | 9/1987 | Taylor et al. ............ 428/137 |
| 4,692,371 | 9/1987 | Morman ............ 428/224 |
| 4,707,398 | 11/1987 | Boggs ............ 428/224 |
| 4,715,857 | 12/1987 | Juhasy et al. ............ 604/359 |
| 4,724,184 | 2/1988 | Killian ............ 428/227 |
| 4,741,949 | 5/1988 | Morman ............ 428/224 |
| 4,755,178 | 7/1988 | Insley et al. ............ 604/367 |
| 4,755,178 | 7/1988 | Insley et al. ............ 428/288 |

FOREIGN PATENT DOCUMENTS

| | | |
|---|---|---|
| 212284 | 3/1987 | European Pat. Off. . |
| 0156649 | 4/1987 | European Pat. Off. . |
| 1575830 | 5/1977 | United Kingdom . |
| 2151272 | 7/1985 | United Kingdom . |
| 2151272A | 7/1985 | United Kingdom . |

OTHER PUBLICATIONS

Wente, Van A. — Superfine Thermoplastic Fibers *Ind. Eng. Chem.* vol. 48, pp. 1342 et seq. (1956).

J. W. S. Hearle, Physical Properties of Textile Fibers, Butterworth, London 1975, pp. 399–403.

Morton, W. E., Physical Properties of Textile Fibers, 2nd edition, John Wiley and Sons, New York (1975), pp. 399–401.

*Primary Examiner*—James C. Cannon
*Attorney, Agent, or Firm*—Donald M. Sell; Walter N. Kirn; Carole Truesdale

[57] ABSTRACT

An elastomeric nonwoven absorbent web is provided. The web comprises a nonwoven fibrous matrix of elastomeric melt-blown small diameter fibers and absorbent staple fibers or absorbent particulate material, wicking staple fibers, and bulking staple fibers dispersed throughout the matrix. This web is particularly useful in an absorbent elastomeric wound dressing. The wound dressing has a fluid permeable, compliant, low adherency wound contacting layer, an intermediate conformable, fluid-absorbent element, i.e., the elastomeric nonwoven absorbent web, and a soft, compliant cover layer.

27 Claims, No Drawings

ABSORBENT ELASTOMERIC WOUND DRESSING

This is a continuation of application Ser. No. 07/194,082 filed May 13, 1988, and now abandoned.

BACKGROUND OF THE INVENTION

1. Field of the Invention

The present invention relates to absorbent elastomeric wound dressings which provide rapid absorption, good wicking, and high liquid retention. Background Information A wound dressing having high sorbency and retention, high conformability, low density, and good wicking, and which is non-linting and economical has long been desired. Gauzes are today the most common wound dressing, but gauzes are expensive to make and exhibit some linting which is undesirable. Many attempts have been made to find a substitute for gauzes, but until now, no fully satisfactory substitute has been found.

One effort in absorbent products has involved incorporating absorbent additives in a fibrous web. Dressings capable of rapid uptake of wound exudate and subsequent retention of those fluids typically rely on absorptive media having low solidity or high void volume. Unfortunately, high void volume webs typically have low strength and hence poor integrity, a combination which generally results in the dressing tearing apart and leaving residues in the wound site when the dressing is removed. Additionally, when these dressings tear or are compressed during removal, they release fluids which have been absorbed, thereby soiling or contaminating patient bedding or clothing.

U.S. Pat. No 3,670,731 (Harmon) discloses the addition of hydrocolloidal particles to a fibrous mass, such as wood pulp, by cascading the particles into the fibrous mass. However, mechanical action causes the particles to dust out.

U.S. Pat. No. 4,366,814 (Riedel) discloses an elastic bandage material for medical tapes and dressing which has at least 50 percent by weight of an extensible porous fabric capable of elongation of at least 30 percent in one direction without tearing and at least 15 percent by weight of an elastomer uniformly impregnated in the fabric and substantially contained on or within the fibers of the fabric without filling the spaces between fibers. The fabric may be of a wide range of synthetic or natural fibers, used singly or in blends. The preferred elastomers include block copolymers, polyurethanes, acrylics, acrylic-olefinic copolymers, and other natural and synthetic rubbers.

U.S. Pat. No. 4,414,970 (Berry) discloses a moisture vapor transmitting elastic bandage which has an inner layer of fabric and an outer layer of fabric bonded to a central layer which is an elastomeric film. The film can be continuous, macroporous or microporous, but is preferably continuous to provide a bacterial barrier. Suitable films which may be obtained in continuous form and which transmit moisture vapor can be made from polyurethane, for example, a thermoplastic polyurethane.

U.S. Pat. No. 4,565,736 (Stein et al.) discloses a surgical compress which is made of an absorptive layer and a covering layer, the covering layer spun or otherwise made of nonwoven hydrophobic, hydrolysis-resistant, aliphatic polyurethane fibers, the covering layer preferably being autogenously bonded to the absorption layer by direct formation of tacky cover layer fibers on the absorption layer.

U.S. Pat. No. 4,715,857 (Juhasz et al.) disclose wound dressings which comprise, in order, a first layer of a permeable material, a layer of a semi-permeable, adhesive material, a charcoal cloth or felt, and a second layer of a permeable material, in which the three layers a substantially co-extensive and surround the charcoal cloth or felt, whereby the first layer of permeable material is bound to the cloth or felt and, around the cloth or felt, to the second layer of permeable material. The layers of permeable material are in the form of a fabric or film and may be of different or, preferably, the same material, examples of suitable materials being natural or synthetic rubber, nylon, polyester, polyurethane and rayon acetate, and other suitable synthetic polymers. The semi-permeable adhesive materials are preferably double-sided transfer tapes.

British Patent Specification No. 1,575,830 (Johnson & Johnson) discloses a flexible and conformable disposable absorbent dressing which comprises a layer of absorbent material, and a thin, flexible, elastic and easily stretchable thermoplastic backing film retained in superimposed relationship with the absorbent layer, the backing film possessing an elastic recovery from 50 percent stretch of at least 75 percent, a rubber modulus of not above 2000 pounds per square inch and a Gurley stiffness at a thickness of 1 mil of not above one. The film is preferably formed from A-B-A block copolymers which consist of A end blocks derived from styrene and B blocks derived from conjugated dienes.

U.S. Pat. No. 4,650,479 (Insley) discloses a sorbent sheet product comprising a coherent fibrous web that includes entangled blown polymeric fibers and high sorbency, liquid sorbent fibers intermingled with the blown polymeric fibers. The blown polymeric fibers may be formed from a wide variety of fiber-forming materials. Representative polymers for forming melt-blown fibers include polypropylene, polyethylene, polyethylene terephthalate, and polyamides.

European Patent Publication No. 0,156,649 (Insley et al.) discloses sorbent sheet products comprising a coherent fibrous web that includes entangled blown fibers and liquid transport fibers intermingled with the blown fibers and an array of solid high sorbency liquid-sorbent polymeric particles uniformly dispersed and physically held within the web. The particles swell upon sorption of liquid, and the transport fibers cause increased and more rapid sorption of liquid by conducting the liquid from external portions of the web to internal portions of the web.

U.S. Pat. No. 4,692,371 (Morman et al.) discloses elastomeric nonwoven webs of elastomeric meltblown fibers, elastomeric films or elastomeric molded materials attained by forming styrenic-(ethylenebutylene)-styrenic block copolymers at elevated temperatures of at least about 90° C. In the case of elastomeric nonwoven webs of elastomeric fibers, other fibers, such as pulp or cellulosic fibers or nonfibrous material such as particulates, may be combined with the elastomeric fibers by known methods.

U.S. Pat. No. 4,692,368 (Taylor et al.) discloses a laminate which is elastic in at least one direction and includes an elastic sheet having at least one nonelastic, nonwoven web joined thereto at least at two areas. The nonelastic web is gathered between the two areas. The elastic sheet is formed from an aromatic polyetherurethane, preferably in the form of melt blown fibers The nonelastic nonwoven web includes spunlaced hydraulically entangled polyester fibers. The nonelastic nonwoven web may also include rayon or wood pulp fibers.

U.S. Pat. No. 4,118,531 (Hauser) discloses a web of blended microfibers and crimped bulking fibers. The web is a lofty resilient web which has high thermal resistance per unit of thickness and moderate weight, as well as other properties which give the web a distinctive utility as thermal insulation.

SUMMARY OF THE INVENTION

This invention provides an elastomeric nonwoven absorbent web, particularly useful in wound dressings, comprising a nonwoven fibrous matrix of elastomeric melt-blown small diameter fibers and absorbent fibers or absorbent particulate material, wicking staple fibers, and bulking staple fibers dispersed throughout the matrix.

This invention further provides an absorbent elastomeric wound dressing comprising (1) a fluid permeable, compliant, low adherency wound contacting layer, (2) an intermediate conformable, fluid-absorbent element, the element having a nonwoven fibrous matrix of elastomeric melt-blown small diameter fibers and absorbent staple fibers or absorbent particulate material, wicking staple fibers, and bulking staple fibers dispersed throughout the matrix, and (3) a soft, compliant cover layer.

The elastomeric webs have excellent wound exudate management properties, good integrity, strength, and the ability to accept extremely high, e.g., 85 weight percent or more, loading levels of secondary fibers and particulate materials. Furthermore, extension or flexing of the webs does not cause the secondary fibers or particulate materials to become dislodged or dust out. Also, the loaded webs retain their conformability even under high loadings.

In addition to having excellent wound exudate management properties, the dressings of the present invention are significantly more elastic and conformable than conventional dressings. This conformability coupled with the high void volume of the dressing allows the dressings to be used as a packing material for cavernous wounds. The integrity of the dressings is such that even when they are used as packings, they are readily removed without tearing and releasing exudates.

DETAILED DESCRIPTION OF THE INVENTION

The wound dressings of the present invention are based on absorbent materials which utilize elastomeric nonwoven webs as a delivery matrix for a variety of vehicles useful for wound management. Exemplary elastomeric materials which can be used to prepare the nonwoven elastomeric webs include polyurethane elastomeric materials, polyester elastomeric materials, polyamide elastomeric materials, and A-B-A block copolymer materials where the A end groups are styrenic moieties and B is an elastomeric midblock. Particularly preferred are polyurethane elastomeric materials. The nonwoven elastomeric webs are preferably formed as a melt-blown web of small diameter fibers as described, for example, in Wente, Van A. "Superfine Thermoplastic Fibers," in Industrial Engineering Chemistry, Vol. 48, pages 1342 et seq (1956). The elastomeric meltblown small diameter fibers preferably have an average diameter of about 5 to 30 microns. Preferably the elastomeric melt-blown small diameter fibers are present in the elastomeric nonwoven absorbent web in an amount of about 10 to 20 weight percent, more preferably about 12 to 18 weight percent.

Retention of exudate fluids is accomplished by loading water-insoluble, water-absorbing, super absorbent particles or absorbent staple fibers which rapidly absorb and retain under pressure large quantities of liquids into the web. The preferred super absorbent particles include modified starches, examples of which are described in U.S. Pat. No. 3,981,100, and high molecular weight acrylic polymers containing hydrophilic groups. A wide variety of such water-insoluble, water-absorbing particles are commercially available and they typically absorb 20 or more times their weight of water, preferably 100 or more times their weight of water. In general, the absorbent particles should absorb at least their own weight of liquid. The sorbent particles may vary in size, at least from 50 to 3000 micrometers in average diameter. Preferably, the particles are between 75 and 1500 micrometers in average diameter.

Preferably, when the absorbent material is super absorbent particulate material, the particulate is present in the delivery matrix in amounts of about 5 to 20 weight percent, more preferably 10 to 20 weight percent of the total weight of the absorbent nonwoven web.

Fibers useful as absorbent staple fibers in the present invention are those having an absorbency of at least 1000% when tested according to ASTM Test Method D-117. To achieve high liquid absorbency and good liquid retention under pressure, the absorbent staple fiber should have at least one outside portion of highly hydrophilic material. Examples of such highly hydrophilic fibers are those prepared by treating acrylonitrile fibers with an alkali metal hydroxide to form a hydrophilic crosslinked polymer on the surface thereof as disclosed in U.S. Pat. No. 4,366,206 and U.S. Pat. No. 4,374,175. Also useful are fibers having a sorbent coating such as a crosslinked, saponified copolymer of methacrylic acid and ethacrylic acid or a homopolymer of acrylic acid. A particularly useful fiber is Lanseal TM F, an acrylonitrile fiber having a hydrophilic crosslinked polymer on the surface thereof, available from Japan Exlan Co., Ltd., Osaka, Japan.

The size of the absorbent staple fibers is preferably in the range of about 0.5 to 50 denier, more preferably about 1 to 30 denier. The size of the sorbent staple fibers depends on the end use of the product with absorbent staple fibers of lower denier providing a softer hand. Preferably, the fibers have an average length in the range of about 2 to 15 centimeters, more preferably less than about 7 to 10 centimeters. The absorbent staple fibers may be crimped to provide additional freedom of expansion to the product during liquid absorption as well as bulk and resilience.

When the absorbent material used in the nonwoven absorbent web is absorbent staple fiber, the fiber is preferably present in an amount of about 10 to 30 weight percent of the total nonwoven absorbent web, more preferably about 17 to 27 weight percent of the total nonwoven absorbent web. Of course, a combination of super absorbent particles and absorbent fibers can be used to provide absorptive capacity in the nonwoven absorbent web.

Wound exudate management properties can be enhanced by further loading the nonwoven absorbent web with hydrophilic wicking fiber to facilitate movement of the exudate fluids from the wound surface into the central absorbing element of the dressing. Fibers useful as wicking fibers are staple fibers having a water retention value of at least about 10%, preferably about 20%, and more preferably about 25% when tested according to ASTM Test Method D2402. Fibers which can be used as wicking fibers include, for example, rayon or cotton staple fibers. Particularly preferred wicking fibers are Absorbit TM rayon staple fiber, available from American Enka Company and Avtex TM Regular rayon staple fiber, available from Avtex Corp. Fiber loading levels of from about 30 to about 60 weight percent of the web are preferably used to achieve the desired wicking performance.

In addition to the super absorbent particles or fibers and the wicking fibers, it is also advantageous to incorporate crimped bulking fibers into the absorbent web matrix. The bulking fibers are staple fibers which assist in retaining the open structure of the nonwoven web to facilitate transfer of wound exudate into the matrix and to prevent the absorbed fluids from being forced out of the absorbent web when compressive force is applied to the absorbent nonwoven web. The bulking fibers should, as a minimum, have an average length sufficient to include at least one complete crimp and preferably at least three or four crimps. The bulking fibers preferably have an average length between about 2 and 15 cm, more preferably the bulking fibers are less than about 7–10 cm in length. Preferably, the bulking fibers are moderately stiff, that is, have a flexural rigidity of $1.5 \times 10^4$ gram-square centimeters per tex or more (as defined by W. E. Morton and J. W. S. Hearle, *Physical Properties of Textile Fibers,* 2nd edit., Wiley, N.Y., 1975, pp. 399–403).

Useful crimped bulking fibers include, for example, acrylic, polyester, nylon, polyolefin, rayon and acetate fibers. Polyester and acrylic fibers are particularly preferred. The crimped bulking fibers are preferably incorporated at loading levels of from about 10 to 30 weight percent of the absorbent nonwoven web.

In addition to the staple fibers, i.e., the absorbent staple fibers, the wicking staple fibers and the bulking staple fibers, and particulate materials used for exudate management considerations, other fibers or particulate matter may be incorporated into the absorbing matrix for the purpose of controlling odors and providing anti-bacterial activity to the dressing. Such other fibers or particulate matter preferably comprise less than about 30 weight percent of the elastomeric nonwoven absorbent web.

The various particulate materials and staple fibers to be incorporated into the elastomeric nonwoven absorbent web can be incorporated by well known methods such as are described in U.S. Pat. No. 4,755,178, (Insley), which is incorporated by reference herein for that purpose.

Preferably, the nonwoven absorbent webs of the invention have a softness value of less than about 80 g, more preferably less than about 60 g, most preferably less than about 50 g, when tested according to INDA Test Procedure 90.0-75, using a slot width of 10 mm. Preferably, the nonwoven absorbent webs have a wicking rate of at least about 0.5 cm, more preferably at least about 1.5 cm, most preferably at least about 2 cm, when tested according to INDA Test Procedure 10.3-70. Preferably, the nonwoven absorbent webs have an absorbency of at least about 1000%, more preferably at least about 1200%, most preferably at least about 1300%, when tested according to ASTM Test Method D 117 or D-461 using a 1% saline solution. Preferably, the nonwoven absorbent webs of the invention have a fluid retention value of at least about 50%, more preferably at least about 55%, most preferably at least about 60%, when tested according to ASTM Test Method D 461 using a 1% saline solution and a 475 g roller.

A variety of materials can be used for the fluid permeable, compliant, low adherency wound contacting layer of the absorbent dressings of the present invention. This wound contacting layer should be sufficiently permeable to permit good flow of wound exudate through the layer and into the nonwoven absorbent layer. Fluid flow must be sufficient to prevent fouling of the exudate under the dressing wound contact layer. Materials useful for the wound contacting layer include, for example, small fiber diameter melt-blown nonwoven webs, porous polyethylene films, woven nylon fabrics, perforated polyethylene film and blown microfiber polypropylene webs. The wound contacting layer of the absorbent wound dressing is preferably coextensive with the nonwoven absorbent web.

Materials suitable for use as the a soft, compliant cover layer or non-wound contacting layer of the absorbent dressings of the present invention preferably have high moisture vapor permeability and low liquid permeability. Such materials include, for example, high moisture vapor permeable films, porous foam material and nonwoven webs. The cover layer can be of the same material as the wound contacting material or other materials such as pressure-sensitive adhesive coated materials. The cover layer may be coextensive with the wound contacting and nonwoven absorbent web or, when the cover layer is coated with a pressure-sensitive adhesive material, the cover layer may extend beyond the dimensions of the wound contacting and absorbent layers to provide a means for securing the dressing over the wound site. In the event that the cover layer does not extend beyond the wound contacting and absorbent layers, the dressing can be secured over the wound with a cohesive wrap or tape.

This invention is further illustrated by the following examples, but the particular materials and amounts thereof recited in these examples, as well as other conditions and details, should not be construed to unduly limit this invention.

In the examples, all parts and percentages are by weight unless otherwise specified. The following test methods were used for evaluation purposes in the examples:

Softness value: INDA Test Procedure 90.0-75, using a slot width of 10 mm;
Wicking rate: INDA Test Procedure 10.3-70.
Absorbency: ASTM Test Method D 117 or D-461 using a 1% saline solution; and
Fluid retention value: ASTM Test Method D 461 using a 1% saline solution and a 475 g roller.

EXAMPLES 1–19

In Example 1, an elastomeric, nonwoven, absorbent, melt-blown, microfiber web was prepared using thermoplastic elastomeric polyurethane polymer (PS 455-203, a polyesterurethane available from K. J. Quinn Co., Malden, Mass.) as the delivery matrix, and a fiber blend of 15 weight percent absorbent fiber (Lanseal TM F, 2.5 denier, 51 mm staple length, available from Japan Exlan Co., Ltd., Osaka, Japan), 70 weight percent wicking fiber (Avtex TM Regular, a rayon fiber, 15 denier, 40 mm staple length, available from Avtex Corp., and 15 weight percent bulking fiber (Orlon TM Type TO 670, 3 denier, 38 mm staple length, available from Du-Pont Co.).

The webs were prepared using a melt blowing process similar to that taught in U.S. Pat. No. 4,188,531 (Hauser) except that the melt-blowing die had circular smooth surfaced orifices (10/cm) with a 5:1 length-to-diameter ratio. The die temperature was maintained at 220° C., the primary air temperature and pressure were, respectively, 230° C. and about 150 kPa, ( 0.63 mm gap width), and the polymer throughput rate was 450 gm/hr/cm. The resulting web had a basis weight of 120 g/m² and contained 18.3 weight percent polyurethane microfiber having a fiber size of 5 to 10 microns and 81.7 weight percent staple fibers.

In Examples 2-19, elastomeric nonwoven absorbent webs were prepared as in Example 1, except that the staple fiber content and basis weight were varied as set forth in Table I. In addition to the Lanseal TM F, rayon, and Orlon TM (identified in Table I as L-F, R, and O, respectively), SA 700, an absorbent web available from Arco, Philadelphia, Pa. and Lanseal TM FA, 3 denier, 51 mm staple length, an odor and fluid absorbent fiber available from Japan Exlan Co., Ltd., Osaka, Japan (identified in Table I as Arco and L-FA, respectively) were used in these examples. The total basis weight of the elastomeric nonwoven absorbent webs are also set forth in Table I.

TABLE I

| Example | Microfiber (wt %) | Staple Fiber Blend Content (weight percent) | | | | | Basis weight (g/m₂) |
|---|---|---|---|---|---|---|---|
| | | L-F | Arco | L-FA | R | O | |
| 1 | 18.3 | 15 | — | — | 70 | 15 | 120 |
| 2 | 17.6 | 15 | — | — | 60 | 25 | 125 |
| 3 | 19.3 | 15 | — | — | 60 | 25 | 114 |
| 4 | 16.9 | 20 | — | — | 60 | 20 | 130 |
| 5 | 12.9 | 20 | — | — | 60 | 20 | 170 |
| 6 | 16.7 | — | 20 | — | 60 | 20 | 132 |
| 7 | 13.2 | — | 20 | — | 60 | 20 | 167 |
| 8 | 16.7 | — | 30 | 10 | 40 | 20 | 135 |
| 9 | 13.7 | — | 30 | 10 | 40 | 20 | 160 |
| 10 | 17.5 | 30 | — | 20 | 35 | 15 | 126 |
| 11 | 12.8 | 30 | — | 20 | 35 | 15 | 172 |
| 12 | 18.2 | 30 | — | 10 | 45 | 15 | 121 |
| 13 | 12.4 | 30 | — | 10 | 45 | 15 | 178 |
| 14 | 17.0 | 20 | — | 10 | 55 | 15 | 129 |
| 15 | 13.6 | 20 | — | 10 | 55 | 15 | 162 |
| 16 | 16.9 | 30 | — | — | 50 | 20 | 130 |
| 17 | 13.5 | 30 | — | — | 50 | 20 | 163 |
| 18 | 16.5 | — | 30 | — | 50 | 20 | 133 |
| 19 | 12.7 | — | 30 | — | 50 | 20 | 173 |

The webs described in Table I were evaluated for softness, wicking, absorbency, absorbency as a function of basis weight and percent retention. Results of these evaluations are reported in Table II. Absorbency and fluid retention were generated with a one percent saline solution. Unreported absorbency data generated with deionized water were approximately 1.5 times the values reported in Table II.

TABLE II

| Example | Softness (g) | Wicking (cm/30 sec) | Absorbency (%) | Absorbency (g/g) | Retention (%) |
|---|---|---|---|---|---|
| 1 | —* | 0.9 | 1070 | 11.7 | — |
| 2 | — | 0.6 | 1220 | 13.3 | — |
| 3 | — | 1.6 | 1170 | 12.7 | — |
| 4 | 30 | 1.4 | 1280 | 13.8 | 60.6 |
| 5 | 55 | 1.8 | 1247 | 13.5 | — |
| 6 | 75 | 2.2 | 1425 | 15.3 | 60.1 |
| 7 | 110 | 2.0 | 1368 | 14.7 | — |
| 8 | 62 | 1.5 | 1470 | 15.8 | 61.2 |
| 9 | 94 | 1.7 | 1341 | 14.6 | — |
| 10 | 29 | 0.7 | 1342 | 14.5 | 60.5 |
| 11 | 39 | 1.0 | 1360 | 14.6 | — |
| 12 | 38 | 1.9 | 1320 | 14.2 | 60.7 |
| 13 | 42 | 1.6 | 1413 | 15.1 | — |
| 14 | 50 | 2.2 | 1247 | 13.5 | 60.9 |
| 15 | 54 | 1.9 | 1363 | 14.6 | — |
| 16 | 48 | 1.7 | 1230 | 13.3 | 60.1 |
| 17 | 54 | 1.5 | 1350 | 14.5 | — |
| 18 | 80 | 2.3 | 1447 | 15.5 | 62.2 |
| 19 | 122 | 1.9 | 1425 | 15.3 | — |

*test not run

As can be seen from the data in Table II, absorbency wicking and softness are variables which are related to the fiber composition and the ratio of these fibers to each other. For example, the Arco fiber definitely makes a stiffer web.

Examples 20-24

In Examples 20-24, elastomeric nonwoven absorbent webs were prepared as in Example 1, except that the elastomeric polyurethane polymer used in Examples 20-22 was PS 440-101, a polyesterurethane thermoplastic elastomeric resin available from K. J. Quinn Co., Malden, Mass., the staple fiber blend contained 15 weight percent Lanseal TM F, 60 weight percent rayon, and 25 weight percent Orlon TM, and the polyurethane fiber diameters, the percent of polyurethane microfiber in the web, and the basis weight of the total absorbent web were as set forth in Table III.

TABLE III

| Example | Microfiber diameter (μ) | Microfiber (wt %) | Basis weight (g/m₂) |
|---|---|---|---|
| 20 | 5-10 | 15.4 | 123 |
| 21 | 22-30 | 16.4 | 126 |
| 22 | 5-10 | 20.0 | 125 |
| 23 | 5-10 | 13.3 | 128 |
| 24 | 22-30 | 16.4 | 122 |

The webs described in Table III were evaluated for softness, wicking, absorbency, absorbency as a function of basis weight and percent retention. Results of these evaluations are reported in Table IV. Absorbency and fluid retention data were generated with a one percent saline solution. Unreported absorbency data generated with deionized water were approximately 1.5 times the values reported in Table IV.

TABLE IV

| Example | Softness (g) | Wicking (cm/30 sec) | Absorbency (%) | Absorbency (g/g) | Retention (%) |
|---|---|---|---|---|---|
| 20 | 44 | 0.6 | 1210 | 13.1 | 61.2 |
| 21 | 52 | 0.7 | 1228 | 13.3 | 60.7 |
| 22 | 41 | 0.6 | 1235 | 13.3 | 63.0 |
| 23 | 48 | 0.6 | 1220 | 13.2 | 62.7 |
| 24 | 56 | 0.7 | 1220 | 13.2 | 61.4 |

As can be seen from the data in Table IV, there is little effect of fiber size on the two polyurethane resins on the critical properties for this dressing. There is an indication that increasing the polyurethane fiber content may actually provide a slightly softer material.

EXAMPLES 25-34

In Examples 25-34, double thicknesses of the elastomeric nonwoven absorbent webs of Examples 10-17 and 24–25, respectively were tested for softness, wicking and absorbency. The results are set forth in Table V.

TABLE V

| Example | Web origin (Example) | Softness (g) | Wicking (cm/30 sec) | Absorbency (%) | Absorbency (g/g) |
|---|---|---|---|---|---|
| 25 | 10 | 90 | 1.6 | 1438 | 15.6 |
| 26 | 11 | 175 | 2.0 | 1469 | 15.9 |
| 27 | 12 | 159 | 2.2 | 1423 | 15.4 |
| 28 | 13 | 371 | 2.3 | 1392 | 15.1 |
| 29 | 14 | 182 | 1.8 | 1496 | 16.2 |
| 30 | 15 | 299 | 1.9 | 1443 | 15.6 |
| 31 | 16 | 115 | 1.0 | 1396 | 15.1 |
| 32 | 17 | 172 | 1.4 | 1425 | 15.4 |
| 33 | 18 | 218 | 2.5 | —* | — |
| 34 | 19 | 311 | 2.0 | — | — |

*test not run

As can be seen from the data in Table V, using two layers of absorbent web has no significant effect on any of the properties except softness which reflects the added thickness vs. the test method limitation.

COMPARATIVE EXAMPLES 1–4

In comparative examples 1–4, commercially available wound dressings were tested for softness, wicking, absorbency, absorbency in relation to basis weight, and percent resiliency. The dressing of Comparative Example 1 was an 8-ply cotton gauze dressing, available from the Kendall Co., Boston, Mass., which had a basis weight of 165 gm/m². The dressing of Comparative Example 2 was a Telfa ™ dressing, available from the Kendall Co., Boston, Mass., which had a basis weight of 197 gm/m². The dressing of Comparative Example 3 was a Melolin ™ dressing, available from Smith & Nephew Medical, Ltd., England, which had a basis weight of 145 gm/m². The dressing of Comparative Example 4 was a Microdon ™ dressing, available from 3M Company, St. Paul, Minn., which had a basis weight of 241 gm/m². Absorbency data collected using deionized water showed essentially no difference from the data collected using one percent saline solution on these samples. The dressings were tested for softness, wicking, absorbency, absorbency in relation to basis weight, and percent resiliency. The results are set forth in Table VI.

TABLE VI

| Comparative Example | Softness (g) | Wicking (cm/30 sec) | Absorbency (%) | Absorbency (g/g) | Retention (%) |
|---|---|---|---|---|---|
| 1 | 58 | 1.0 | 690 | 8.4 | 43 |
| 2 | 75 | 0.3 | 700 | 8.5 | 54 |
| 3 | 90 | 0.4 | 620 | 7.8 | 46 |
| 4 | 130 | 0.4 | 1020 | 11.1 | 56 |

As can be seen from the data in Table VI, absorbency retention and softness do not achieve the levels of the dressing examples of this application. Wicking rate on samples, 2, 3, and 4 is also significantly slower.

The various modifications and alterations of this invention will be apparent to those skilled in the art without departing from the scope and spirit of this invention and this invention should not be restricted to that set forth herein for illustrative purposes.

What is claimed is:

1. An elastomeric nonwoven absorbent web comprising a nonwoven fibrous matrix of about 10 to 20 weight percent elastomeric melt-blown small diameter fibers and about 10 to 30 weight percent absorbent staple fibers or about 5 to 20 weight percent absorbent polymeric particulate material, about 30 to 60 weight percent wicking staple fibers, and about 10 to 30 weight percent crimped bulking staple fibers dispersed throughout the matrix.

2. The elastomeric nonwoven absorbent web of claim 1 wherein said elastomeric melt-blown small diameter fibers comprise polyurethane elastomeric materials, polyester elastomeric materials, polyamide elastomeric materials, A-B-A block copolymer materials where the A end groups are styrenic moieties and B is an elastomeric midblock, and combinations thereof.

3. The elastomeric nonwoven absorbent web of claim 1 wherein said elastomeric melt-blown small diameter fibers comprise polyurethane fibers.

4. The elastomeric nonwoven absorbent web of claim 1 wherein said absorbent staple fibers comprise fibers having an absorbency of at least about 1000%.

5. The elastomeric nonwoven absorbent web of claim 4 wherein said absorbent staple fibers comprise acrylonitrile fibers having a hydrophilic surface.

6. The elastomeric nonwoven absorbent web of claim 1 wherein said wicking staple fibers comprise cotton fibers, rayon fibers, wool fibers, silk fibers, or combinations thereof.

7. The elastomeric nonwoven absorbent web of claim 1 wherein said wicking staple fibers comprise rayon or cotton fibers.

8. The elastomeric nonwoven absorbent web of claim 1 wherein said crimped bulking staple fibers have an average crimp frequency of more than about one-half crimp per centimeter.

9. The elastomeric nonwoven absorbent web of claim 8 wherein said crimp frequency is at least about 2 crimps per centimeter.

10. The elastomeric nonwoven absorbent web of claim 1 wherein said bulking staple fiber has a flexural rigidity of $1.5 \times 10^{-4}$ gram-square centimeters per tex.

11. The elastomeric nonwoven absorbent web of claim 1 wherein said bulking staple fiber is acrylic or polyester fiber.

12. The elastomeric nonwoven absorbent web of claim 1 wherein said web has a softness of less than about 80 g.

13. The elastomeric nonwoven absorbent web of claim 1 wherein said web has a wicking value of at least about 0.5 cm/30 sec.

14. The elastomeric nonwoven absorbent web of claim 1 wherein said web has an absorbency of at least about 1000 percent.

15. The elastomeric nonwoven absorbent web of claim 1 wherein said web has an absorbency of at least 11.5 g per g basis weight.

16. The elastomeric nonwoven absorbent web of claim 1 wherein said web has a retention of absorbed liquid of at least about 50 percent.

17. An absorbent elastomeric wound dressing comprising (1) a fluid permeable, compliant, low adherency wound contacting layer, (2) an intermediate conformable, fluid-absorbent element, the element having a nonwoven fibrous matrix of about 10 to °weight percent elastomeric melt-blown small diameter fibers and about 10 to 30 weight percent absorbent staple fibers or about 5 to 20 weight percent absorbent polymeric particulate material, about 30 to 60 weight percent wicking staple fibers, and about 10 to 30 weight percent crimped bulking staple fibers dispersed throughout the matrix, and (3) a soft, compliant cover layer.

18. The wound dressing of claim 17 wherein said wound contacting layer and said fluid-absorbent element are coextensive.

19. The wound dressing of claim 17 wherein said wound contacting layer is a porous nonwoven small diameter fiber web.

20. The wound dressing of claim 19 wherein said porous nonwoven small diameter fiber web comprises a thermoplastic elastomeric resin.

21. The wound dressing of claim 20 wherein said thermoplastic elastomeric resin is polyurethane.

22. The wound dressing of claim 17 wherein said cover layer is absorbent liquid impermeable and moisture vapor permeable.

23. The wound dressing of claim 22 wherein said cover layer comprises a nonwoven small diameter fiber web.

24. The wound dressing of claim 22 wherein one face of said cover layer comprises a pressure-sensitive adhesive layer for contact with said fluid absorbent element.

25. The wound dressing of claim 22 wherein said cover layer extends beyond said fluid-absorbent element and said wound contacting layer.

26. An elastomeric nonwoven absorbent web comprising a nonwoven fibrous matrix of about 10 to 20 weight percent polyurethane melt-blown small diameter fibers and about 10 to 30 weight percent absorbent staple fibers or about 5 to 20 weight percent absorbent polymeric particulate material, about 30 to 60 weight percent wicking staple fibers, and about 10 to 30 weight percent crimped bulking staple fibers dispersed throughout the matrix.

27. An elastomeric nonwoven absorbent web comprising a nonwoven fibrous matrix of about 10 to 20 weight percent polyurethane melt-blown small diameter fibers and about 10 to 30 weight percent absorbent staple fibers or about 5 to 20 weight percent absorbent polymeric particulate material, about 30 to 60 weight percent wicking staple fibers, and about 10 to 30 weight percent crimped bulking staple fibers dispersed throughout the matrix, said web having a softness of less than about 80 g, a wicking value of at least about 0.5 cm/30 sec, and absorbency of at least about 1000 percent and at least 11.5 g per g basis weight, and a retention of absorbed liquid of at least about 50 percent.

* * * * *

UNITED STATES PATENT AND TRADEMARK OFFICE
CERTIFICATE OF CORRECTION

PATENT NO.   : 4,957,795
DATED        : September 18, 1990
INVENTOR(S)  : John E. Riedel It is certified that error appears in the above-identified patent and that said Letters Patent is hereby corrected as shown below:

Col. 2, line 7     at end of line, delete "a" and insert -- are --

Col. 2, line 57     "90°C" should read -- 290°C --

Col. 5, line 29     "$1.5 \times 10^4$" should read -- $1.5 \times 10^{-4}$ --

Col. 6, line 68     "TO" shuld read -- OT --

Col. 7, line 35     Example 3 should read across as follows:
3    19.3    -    15    -    60    25    114

Col. 10, line 63     delete "°" and insert "20" so line reads: -- . . . about 10 to 20 weight percent --

Signed and Sealed this

Fourth Day of February, 1992

Attest:

HARRY F. MANBECK, JR.

*Attesting Officer*                 *Commissioner of Patents and Trademarks*